United States Patent [19]

Isogai et al.

[11] 4,355,173

[45] Oct. 19, 1982

[54] PROCESS FOR THE PREPARATION OF ALKYL CARBOXYLATE

[75] Inventors: Nobuo Isogai; Takashi Okawa; Motoyuki Hosokawa; Natsuko Wakui; Toshiyasu Watanabe, all of Niigata, Japan

[73] Assignee: Mitsubishi Gas Chemical Company, Inc., Tokyo, Japan

[21] Appl. No.: 269,686

[22] Filed: Jun. 2, 1981

[30] Foreign Application Priority Data

Jun. 9, 1980 [JP] Japan .................................. 55-77386

[51] Int. Cl.³ ............................................. C07C 69/76
[52] U.S. Cl. .................................. 560/103; 560/231; 560/232; 560/265; 260/410.9 R
[58] Field of Search ............... 560/103, 232, 231, 265; 260/410.9 R

[56] References Cited

U.S. PATENT DOCUMENTS 4,189,441  2/1980  Braca et al. ............................ 560/232

FOREIGN PATENT DOCUMENTS 2731962  2/1979  Fed. Rep. of Germany .
2831354  1/1980  Fed. Rep. of Germany .
54-59212  5/1979  Japan .

OTHER PUBLICATIONS

J. Am. Chem. Soc., 100:19, Sep. 13, 1978, pp. 6238–6240.

Primary Examiner—Paul J. Killos
Attorney, Agent, or Firm—Frishauf, Holtz, Goodman & Woodward

[57] ABSTRACT

A commercially acceptable and advantageous process for the preparation of an alkyl carboxylate having the formula $R^1COOCH_2R^2$ by reacting an alkyl carboxylate having the formula $R^1COOR^2$, carbon monoxide and hydrogen is disclosed ($R^1$ is hydrogen, alkyl group or aromatic group and $R^2$ is alkyl group). The reaction is conducted by the concurrent use of manganese and ruthenium as catalyst in the presence of iodine or bromine as the promoter. The reaction proceeds smoothly under milder condition in high yield and high selectivity.

25 Claims, No Drawings

PROCESS FOR THE PREPARATION OF ALKYL CARBOXYLATE

BACKGROUND OF THE INVENTION

1. Field of the Invention

This invention relates to a commercially advantageous process for the preparation of an alkyl carboxylate represented by the general formula $R^1COOCH_2R^2$ by homologation reaction from an alkyl carboxylate represented by the general formula $R^1COOR^2$, wherein $R^1$ represents a hydrogen atom, an alkyl group or an aromatic group and $R^2$ represents an alkyl group.

The homologation reaction of an alkyl carboxylate of this invention can be shown by the following general scheme:

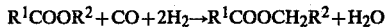

$$R^1COOR^2 + CO + 2H_2 \rightarrow R^1COOCH_2R^2 + H_2O$$

(wherein $R^1$ is a hydrogen atom, a normal or branched chain alkyl group with 1 to 10 carbon atoms, or an aromatic group with 6 to 14 carbon atoms and $R^2$ is a normal or branched chain alkyl group with 1 to 5 carbon atoms).

The alkyl carboxylates which can be prepared by this reaction may be exemplified by ethyl acetate which has a wide commercial use.

2. Description of the Prior Art

Ethyl acetate has been heretofore prepared by low-temperature condensation of acetaldehyde by the use of a catalyst such as an aluminum alcoholate. On the other hand, two processes for direct preparation of ethyl acetate have been recently proposed: one is the reaction of methyl acetate with carbon monoxide and hydrogen by using Fe, Co, Ru or Rh as catalyst (Japanese Patent Disclosure No. 59212/1979), and the other is the simultaneous reaction of dimethyl ether and methyl acetate or reaction of methyl acetate with carbon monoxide and hydrogen by using Ru as catalyst (J. Am. Chem. Soc., 100, 6238 (1978)). In view of the expected future shortage of petroleum resources and taking in consideration the fact that the preparation of methyl acetate starting material may not be necessarily dependent upon petroleum products, these processes may be regarded as superior to the process which use acetaldehyde as starting material which is usually derived from ethylene.

The former process utilizes a catalyst such as cobalt or iron in the presence of a halogen, a halide, a phosphine, or an amine as the promoter, but has the disadvantage that the reaction should be performed under drastic conditions because of the low activity of the catalyst. For example, when cobalt acetate is used as the catalyst in the presence of iodine, to obtain a practical reaction rate at a reaction temperature of within the range of 150°–220° C., it is necessary to use extremely high pressure, e.g. up to 1200 Kg/cm². On the other hand, in the latter process which utilizes diiodotetracarbonylruthenium(II) complex ($RuI_2(CO)_4$) or tris-(acetylacetonate)ruthenium(III) complex as the catalyst in the presence of an iodine compound, the reaction proceeds at a slower rate than the former process, and only an extremely low space-hourly yield is attainable. Moreover, when dimethyl ether and methyl acetate are used concurrently as the starting materials, the process tends to become complex in order to separate and recover the unreacted starting materials.

As described above, in the practice of the reaction of methyl acetate or dimethyl ether with carbon monoxide and hydrogen by the processes known in the art, the largest problem is the extremely low reaction rates of these reactions in comparison with usual carbonylation or homologation reactions of methanol and development of a catalyst which may be employed on a commercial basis has been earnestly desired.

SUMMARY OF THE INVENTION

We have conducted intensive research toward development of a highly active catalyst which allows the homologation reaction of an alkyl carboxylate to proceed at a sufficient reaction rate and with high selectivity to give the alkyl ester, the alkyl group thereof being extended by one methylene unit when compared to the alkyl group of the alkyl carboxylate starting material, of the corresponding carboxylic acid, and have succeeded in completing the present invention by the discovery that the objects stated above can be successfully realized by the concurrent use of manganese and ruthenium as the main catalyst in the presence of a promoter selected from the group consisting of iodine, bromine, a compound of them and a mixture thereof.

Thus, the object of this invention is to provide a commercially acceptable and advantageous process for the preparation of an alkyl carboxylate by homologation reaction from an alkyl carboxylate starting material, the alkyl group contained in the product has an extra methylene group compared to that of the starting material.

The present invention thus relates to a process for the preparation of an alkyl carboxylate represented by the general formula $R^1COOCH_2R^2$ by reacting an alkyl carboxylate starting material represented by the general formula $R^1COOR^2$, carbon monoxide and hydrogen, characterized in that manganese or a manganese compound and ruthenium or a ruthenium compound are used concurrently as the main catalyst and iodine, bromine or a compound of iodine or bromine is used as the promoter, wherein $R^1$ represents a hydrogen atom, a normal or branched chain alkyl group with 1 to 10 carbon atoms or an aromatic group with 6 to 14 carbon atoms and $R^2$ represents a normal or branched chain alkyl group with 1 to 5 carbon atoms.

DETAILED DESCRIPTION OF THE INVENTION

The alkyl carboxylate employed as the starting material of the present invention is an alkyl ester of a normal or branched chain aliphatic carboxylic acid with 1 to 11 carbon atoms or an aromatic carboxylic acid with 7 to 15 carbon atoms, the said alkyl group is a normal or branched chain alkyl group with 1 to 5 carbon atoms, and may be exemplified by methyl formate, methyl acetate, ethyl acetate, methyl propionate, methyl n-butylate, methyl i-butylate, methyl benzoate, methyl toluate, methyl dimethylbenzoate, etc.

The product obtainable from the above is ethyl formate, ethyl acetate, propyl acetate, ethyl propionate, ethyl n-butylate, ethyl i-butylate, ethyl benzoate, ethyl toluate, ethyl dimethylbenzoate, etc., respectively.

An additional advantage obtainable by the process of this invention is that the by-production of a higher homologue is scarecely detected. Contrary to the above, in the process described in the Japanese Patent Disclosure aforementioned, the by production of the a higher homologue is substantial.

The concurrent use of manganese and ruthenium as the main catalyst is indispensable in the present invention and no practical catalyst activity is observed when manganese or ruthenium alone is combined with a promoter such as iodine or bromine.

It is a completely unpredictable fact that a manganese compound shows a significant effect for catalyzing the homologation reaction when combined with the other catalyst component, i.e. ruthenium and a promoter, i.e. iodine, bromine or compounds thereof, since it has reported in any publication that a manganese compound can catalyze OXO reaction which is a somewhat similar reaction to the process of this invention.

Besides manganese metal and manganese carbonyl compounds, manganese salts of an organic acid such as manganese formate, manganese acetate, manganese n-butyrate, manganese benzoate and manganese naphthenate, manganese(II) and (III) acetylacetonate, or inorganic manganese compounds such as manganese dioxide, manganese carbonate and manganese chloride, can be used as the source of the manganese catalyst of the present invention. A mixture of them can also be used. Any ruthenium compound can be used as the source of the ruthenium catalyst, and can be exemplified by halides, oxides, carbonyl complexes, acetylacetonate complexes, phosphides, etc. A mixture thereof can also be used. The use of readily available manganese(II) acetate and ruthenium chloride is commercially preferred.

For an advantageous practice of the process of the present invention, the quantity of the catalyst employed is within a range of 0.0001-0.1 mole, preferably 0.005-0.05 mole of a manganese catalyst and 0.0001-0.05 mole, preferably 0.001-0.02 mole of a ruthenium catalyst respectively per 1 mole of alkyl carboxylate starting material. The reaction rate is lowered by the use of a smaller amount of the catalyst than that specified above and the use of a larger quantity of the catalyst than that specified above is uneconomical, though no adverse effect is observed. A sufficiently satisfactory excellent catalyst activity can be realized by the concurrent use of both the catalysts, i.e. Mn and Ru, within the range specified above when combined with a promoter mentioned hereinafter.

Iodine or bromine is used as the promoter of the present catalyst system. Methyl iodide, sodium iodide, potassium iodide, lithium iodide, iodic acid, hydrogen iodide, etc. can be shown as examples of the iodine source and iodine bromide, methyl bromide, sodium bromide, potassium bromide, hydrogen bromide, etc. can be shown as examples of the bromine source. A mixture of these compounds can also be used. The quantity of iodine, bromine, or their compounds employed is within a range of 0.001-0.1 mole and preferably 0.005-0.05 mole per 1 mole of alkyl carboxylate starting material. The quantity within the range described above is practical because the use of a smaller amount tends to lower the reaction rate and the use of a larger amount is uneconomical.

The reaction temperature of the process of the present invention is within the range of 140°-300° C. and a temperature within the range of 160°-250° C. is preferred. Stoichiometrically, in the process of this invention, the use of a gas mixture of carbon monoxide and hydrogen having a molar ratio of $CO/H_2 = \frac{1}{2}$ is required, but wide variety of synthesis gases with the molar ratio of carbon monoxide and hydrogen ranging from 10/1 to 1/10 can be used. Relative to the reaction pressure, it is necessary to use a pressure of not less than 50 $Kg/cm^2$ and there is no need to limit the upper end but usually the upper end is 600 $Kg/cm^2$ and a pressure of 100-400 $Kg/cm^2$ is preferred for practical operation. In the process of this invention, the reaction time is within the range of 10 minutes-5 hours and preferably 0.5-3 hours.

Although the use of a solvent is not required for the process of the present invention, if it is desired to use a solvent, a saturated aliphatic hydrocarbon such as n-hexane, n-heptane, n-octane or cyclohexane, an aromatic hydrocarbon such as benzene, toluene, xylene or ethylbenzene, or a cyclic ether such as tetrahydrofuran or dioxane can be used as the solvent. Moreover, a carboxylic acid and/or an alcohol which correspond to the carboxylic acid moiety and/or alcohol moiety of the alkyl carboxylate starting material may be used.

According to the present invention, an alkyl carboxylate reacts with carbon monoxide and hydrogen under milder conditions and at a higher reaction rate than by the processes heretofore known to the art, to give, selectively and in high yield, the alkyl ester with an additional methylene unit, of the corresponding carboxylic acid. Hence, the present invention possesses a high commercial value because ethyl acetate, for example, can be prepared economically and advantageously from methyl acetate.

The practice of the present invention is not limited to a batch process, and can be advantageously adopted to a semi-batch process or a continuous process.

In a continuous process, the residence time in the homologation reactor can be deemed as the reaction time. In the reaction, it is desired that liquid phase and vapor phase should be contacted sufficiently and therefore, adoption of a means for improving the vapor-liquid contact such as an agitator or a packed bed etc. is desired.

DESCRIPTION OF THE PREFERRED EMBODIMENTS

The present invention is explained in more detail by the Examples described below. It is to be noted that the following Examples are given only for illustration of the process of this invention and are not construed to limit the scope of the present invention.

EXAMPLE 1

Methyl acetate 20 g, sodium iodide 1 g, manganese acetate ($Mn(CH_3CO_2)_2.4H_2O$) 1 g and ruthenium chloride ($RuCl_3$) 0.1 g were charged into a 100 ml Hastelloy autoclave equipped with shaking apparatus, and the autoclave was closed. Then, a gas mixture of hydrogen and carbon monoxide ($H_2/CO = 1$) was charged into the autoclave through a gas nozzle to give a pressure of 200 $Kg/cm^2$, and the autoclave was sealed. The mixture was allowed to react at 200° C. for 3 hours.

After the reaction, the autoclave was cooled and the residual gas was purged. Analysis by gas chromatography of the liquid reaction product showed that the conversion of methyl acetate was 55.3 mole % and the selectivity to ethyl acetate was 77.3 mole %. Besides methyl acetate and ethyl acetate, it was found that methanol, ethanol and acetic acid which were formed by hydrolysis of the esters were present in the liquid reaction products, too. The methyl group balance of the reaction product based on charged methyl acetate was 99.1 mole %, which was calculated by the equation shown below:

Methyl group balance (mole %) =

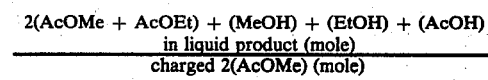

In the equation, Ac means acetyl group, Me means methyl group and Et means ethyl group. Analysis by gas chromatography showed that by-production of higher homologues, e.g. propyl acetate, butyl acetate, etc. and the hydrolysis products thereof was less than 0.1wt. %. The results are summarized in Table 1.

EXAMPLES 2–8

Various alkyl carboxylates were treated by a process similar to Example 1 by the use of various kinds and amounts of the main catalyst or promoter, and under various conditions. In Example 7, the methyl group balance was calculated by the following formula:

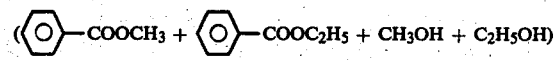

The results are summarized in Table 1.

CONTROL EXAMPLES 1–3

In Control Examples 1–3, manganese compound or ruthenium compound alone was used as the catalyst and the other reaction conditions were the same as those of Example 1. The results are summarized in Table 2. It is clear from Table 2 that practically no ethyl acetate was formed from the reaction of methyl acetate with carbon monoxide and hydrogen when manganese acetate, manganese carbonyl or ruthenium chloride alone was used as the catalyst.

CONTROL EXAMPLE 4

An experiment was conducted by using cobalt acetate-ruthenium chloride-sodium iodide catalyst system. The other reaction conditions were the same as those of Example 1. The result is given in Table 2. It is clear that the result of this experiment is inferior to the results obtained in Examples 1–8 relative to the selectivity to the desired product.

TABLE 1

| Example No. | Charged ester (g) | Main Catalyst (g) | Promoter (g) | H₂/CO (Molar ratio) | Pressure (Kg/cm²) | Temperature (°C.) | Time (hr) | Conversion (mole %) | Selectivity to product (mole %) | Methyl group balance (mole %) |
|---|---|---|---|---|---|---|---|---|---|---|
| 1 | Methyl acetate 20 | Mn(AcO)₂.4H₂O 1 RuCl₃ 0.1 | NaI 1 | 1:1 | 200 | 200 | 3 | 55.3 | Ethyl acetate 77.3 | 99.1 |
| 2 | Methyl acetate 20 | Mn(AcO)₂.4H₂O 0.4 RuCl₃ 0.5 | NaI 0.5 | 1:1 | 120 | 200 | 3 | 36.1 | Ethyl acetate 72.7 | 98.7 |
| 3 | Methyl acetate 20 | Mn₂(CO)₁₀ 0.4 RuCl₃ 0.1 | NaI 1 | 2:1 | 210 | 180 | 2 | 49.0 | Ethyl acetate 80.1 | 100 |
| 4 | Methyl acetate 20 | Mn(AcO)₂.4H₂O 1 Ru₃(CO)₁₂ 0.2 | CH₃I 1 | 2:1 | 210 | 200 | 3 | 39.9 | Ethyl acetate 63.8 | 98.8 |
| 5 | Methyl acetate 20 | Mn(Acac)₂ 1 RuO₄ 0.2 | IBr 0.5 | 1:1 | 200 | 180 | 2 | 48.8 | Ethyl acetate 60.3 | 95.5 |
| 6 | Ethyl acetate 20 | Mn(AcO)₂.4H₂O 1 RuCl₃ 0.1 | NaI 1 | 1:1 | 200 | 200 | 3 | 22.2 | Propyl acetate 50.5 | — |
| 7 | Methyl benzoate 20 | Mn₂(CO)₁₀ 0.4 RuCl₃ 0.2 | NaI 1 | 1:1 | 200 | 220 | 2 | 28.3 | Ethyl benzoate 48.2 | 98.2 |
| 8 | Methyl acetate 20 | Mn₂(CO)₁₀ 0.4 RuCl₃ 0.5 | NaBr 1 | 1:1 | 200 | 210 | 4 | 30.2 | Ethyl acetate 48.5 | 96.1 |

In the Table Mn(AcO)₂ means manganese acetate and Mn(Acac)₂ means manganese acetylacetone.

TABLE 2

| Control Example No. | Charged ester (g) | Main Catalyst (g) | Promoter (g) | H₂/CO (Molar ratio) | Pressure (Kg/cm²) | Temperature (°C.) | Time (hr) | Conversion (mole %) | Selectivity to product (mole %) | Methyl group balance (mole %) |
|---|---|---|---|---|---|---|---|---|---|---|
| 1 | Methyl | | | | | | | | Ethyl | |

TABLE 2-continued

| Control Example No. | Charged ester (g) | Main Catalyst (g) | Promoter (g) | $H_2/CO$ (Molar ratio) | Pressure ($Kg/cm^2$) | Temperature (°C.) | Time (hr) | Conversion (mole %) | Selectivity to product (mole %) | Methyl group balance (mole %) |
|---|---|---|---|---|---|---|---|---|---|---|
|  | acetate 20 | RuCl₃ 0.85 Mn(AcO)₂·4H₂O | NaI 1 | 1:1 | 200 | 200 | 3 | 4.7 | acetate 7.6 Ethyl acetate | 98.1 |
| 2 | Methyl acetate 20 | 1 Mn₂(CO)₁₀ | NaI 1 | 1:1 | 200 | 200 | 3 | 11.0 | acetate 4.3 Ethyl acetate | 97.0 |
| 3 | Methyl acetate 20 | 0.4 Co(AcO)₂·4H₂O | NaI 1 | 2:1 | 210 | 180 | 2 | 6.4 | acetate 8.2 Ethyl acetate | 98.2 |
| 4 | Methyl acetate 20 | 1 RuCl₃ 0.1 | NaI 1 | 1:1 | 200 | 200 | 3 | 40.5 | 40.7 | 91.0 |

In the Table Ac means acetyl group.

We claim:

1. A process for the preparation of an alkyl carboxylate of general formula $R^1COOCH_2R^2$ comprising reacting (i) an alkyl carboxylate starting material of the general formula $R^1COOR^2$, (ii) carbon monoxide and (iii) hydrogen, wherein $R^1$ is a hydrogen atom, a normal or branched chain alkyl group having 1 to 10 carbon atoms or an aromatic group having 6 to 14 carbon atoms and $R^2$ is a normal or branched chain alkyl group having 1 to 5 carbon atoms, in the presence of a catalyst comprising (a) manganese or a manganese compound and (b) ruthenium or a ruthenium compound, and a promoter comprising at least one element or compound selected from the group consisting of iodine, bromine and compounds of iodine and bromine, at a temperature of from 140° to 300° C. under a pressure of from 50 to 600 Kg/cm², said carbon monoxide and hydrogen being in a molar ratio of $CO/H_2$ of from 1/10 to 10/1.

2. The process as claimed in claim 1, wherein said alkyl carboxylate starting material is selected from the group consisting of methyl acetate, ethyl acetate and methyl benzoate.

3. The process as claimed in claim 1, wherein the amounts of the catalyst and the promoter used per 1 mole of said alkyl carboxylate starting material are within the range of 0.0001–0.1 mole of Mn, 0.0001–0.05 mole of Ru and 0.001–0.1 mole of I or Br.

4. A process as claimed in claim 3, wherein the amounts of the catalyst and the promoter used per 1 mole of said alkyl carboxylate starting material are within a range of 0.005–0.05 mole of Mn, 0.001–0.02 mole of Ru and 0.005–0.05 mole of I or Br.

5. The process as claimed in claim 2, wherein said alkyl carboxylate is methyl acetate.

6. The process as claimed in claim 1, wherein the reaction time is within the range of 10 minutes–5 hours.

7. The process as claimed in claim 6, wherein the reaction temperature is within the range of 160°–250° C., the reaction pressure is within the range of 100–400 Kg/cm² and the reaction time is within the range of 0.5–3 hours.

8. The process as claimed in claim 2, wherein said alkyl carboxylate is methyl benzoate.

9. The process as claimed in claim 1, wherein the reaction is conducted in the absence of a solvent.

10. The process as claimed in claim 1, wherein the reaction is conducted in the presence of a solvent.

11. The process as claimed in claim 10, wherein the solvent is selected from the group consisting of saturated aliphatic hydrocarbons, aromatic hydrocarbons, cyclic ethers and a mixture thereof.

12. The process as claimed in claim 1, wherein the reaction is conducted in the presence of a carboxylic acid and/or an alcohol which corresponds to the carboxylic acid moiety and the alcohol moiety of said alkyl carboxylate starting material, respectively.

13. The process as claimed in claim 1, wherein the reaction is conducted batch-wise.

14. The process as claimed in claim 1, wherein the reaction is conducted semibatch-wise.

15. The process as claimed in claim 1, wherein the reaction is conducted continuously.

16. The process as claimed in claim 1, wherein the reaction is conducted by using a means for improving the vapor-liquid contact.

17. The process as claimed in claim 2, wherein the reaction is conducted by using 0.0001–0.1 mole of Mn, 0.0001–0.05 mole of Ru and 0.001–0.1 mole of I or Br per 1 mole of said alkyl carboxylate starting material, for 10 minutes–5 hours.

18. The process as claimed in claim 17, wherein the reaction is conducted by using 0.005–0.05 mole of Mn, 0.001–0.02 mole of Ru and 0.005–0.05 mole of I or Br per 1 mole of said alkyl carboxylate starting material, at a temperature of 160°–250° C. under a pressure of 100–400 Kg/cm² for 0.5–3 hours.

19. The process as claimed in claim 5, wherein the reaction is conducted by using 0.005–0.05 mole of Mn, 0.001–0.02 mole of Ru and 0.005–0.05 mole of I or Br per 1 mole of said alkyl carboxylate starting material, at a temperature of 160°–250° C. under a pressure of 100–400 Kg/cm² for 0.5–3 hours.

20. The process as claimed in claim 8, wherein the reaction is conducted by using 0.005–0.05 mole of Mn, 0.001–0.02 mole of Ru and 0.005–0.05 mole of I or Br per 1 mole of said alkyl carboxylate starting material, at a temperature of 160°–250° C. under a pressure of 100–400 Kg/cm² for 0.5–3 hours.

21. The process as claimed in claim 1, wherein the manganese catalyst component (a) is selected from the group consisting of manganese metal, a manganese carbonyl, or organic acid salt of manganese, a manganese acetylacetonate and an inorganic manganese compound; the ruthenium catalyst component (b) is selected from the group consisting of ruthenium metal, a ruthenium carbonyl, a ruthenium acetylacetonate and an inorganic ruthenium compound; and said promoter is selected from the group consisting of elemental iodine or bromine, a metal or hydrogen iodide or bromide, an alkyl iodide or bromide, iodic acid and iodine bromide.

22. The process as claimed in any one of claims 19, 20, 1, 21, 2, 3, 4, 5, 7, 11, 12, 17 or 18, wherein the manganese catalyst component (a) is selected from the group consisting of manganese metal, a manganese carbonyl compound, manganese formate, manganese acetate, manganese n-butyrate, manganese benzoate and manganese naphthenate, manganese (II) and (III) acetylacetonate, manganese dioxide, manganese carbonate and manganese chloride, and mixtures thereof; and the ruthenium catalyst component (b) is selected from the group consisting of ruthenium metal and the ruthenium halides, oxides, carbonyl complexes, acetylacetonate complexes, phosphides, and mixtures thereof.

23. The process as claimed in claim 22, wherein said manganese catalyst is manganese (II) acetate.

24. The process as claimed in claim 23, wherein said ruthenium catalyst is ruthenium catalyst.

25. The process as claimed in claim 22, wherein said ruthenium catalyst is ruthenium chloride.

* * * * *